US012605545B2

(12) United States Patent
Haddock et al.

(10) Patent No.: US 12,605,545 B2
(45) Date of Patent: Apr. 21, 2026

(54) TEMPLATE BASED ARTIFACT REDUCTION IN NEUROMODULATION APPLICATIONS

(71) Applicant: Boston Scientific Neuromodulation Corporation, Valencia, CA (US)

(72) Inventors: Andrew Haddock, Los Angeles, CA (US); Sandeep Avvaru, Houston, TX (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 301 days.

(21) Appl. No.: 18/456,306

(22) Filed: Aug. 25, 2023

(65) Prior Publication Data

US 2024/0066298 A1     Feb. 29, 2024

Related U.S. Application Data

(60) Provisional application No. 63/374,011, filed on Aug. 31, 2022.

(51) Int. Cl.
| | |
|---|---|
| *A61N 1/36* | (2006.01) |
| *A61B 5/00* | (2006.01) |
| *A61B 5/388* | (2021.01) |
| *A61N 1/372* | (2006.01) |

(52) U.S. Cl.
CPC .......... *A61N 1/36062* (2017.08); *A61B 5/388* (2021.01); *A61B 5/4836* (2013.01); *A61N 1/36139* (2013.01); *A61N 1/36153* (2013.01); *A61N 1/37247* (2013.01)

(58) Field of Classification Search
None
See application file for complete search history.

(56) References Cited

U.S. PATENT DOCUMENTS

| | | | |
|---|---|---|---|
| 6,181,969 | B1 | 1/2001 | Gord |
| 8,606,362 | B2 | 12/2013 | He et al. |
| 8,620,436 | B2 | 12/2013 | Parramon et al. |
| 9,044,155 | B2 | 6/2015 | Strahl |
| 9,259,574 | B2 | 2/2016 | Aghassian et al. |
| 9,533,148 | B2 | 1/2017 | Carcieri |
| 10,716,937 | B2 | 7/2020 | Feldman et al. |
| 10,792,491 | B2 | 10/2020 | Feldman et al. |
| 10,842,996 | B2 | 11/2020 | Baru et al. |
| 10,881,859 | B2 | 1/2021 | Brill et al. |
| 10,912,942 | B2 | 2/2021 | Weerakoon et al. |

(Continued)

OTHER PUBLICATIONS

Akhoun, Idrick, et al., "Electrically Evoked Compound Action Potential Artifact Rejection by Independent Component Analysis: Technique Validation," Hearing Research, 302, 2013, pp. 60-73.

(Continued)

*Primary Examiner* — Lynsey C Eiseman
(74) *Attorney, Agent, or Firm* — Lewis & Reese, PLLC

(57) ABSTRACT

Methods and systems for recording evoked potentials evoked during electrical stimulation of a patient's neural tissue are disclosed. The methods and systems are useful with treatment modalities, such as spinal cord stimulation (SCS). The disclosed methods and system allow for stimulation artifacts to be reduced in, or removed from, the recorded signals. A residual portion of the stimulation artifact can be modeled and subtracted from a recorded signal that includes both artifact and neural response contributions.

16 Claims, 6 Drawing Sheets

(56)  References Cited

U.S. PATENT DOCUMENTS

| | | | |
|---|---|---|---|
| 10,940,316 | B2 | 3/2021 | Hincapie Ordonez et al. |
| 11,040,192 | B2 | 6/2021 | Weerakoon et al. |
| 11,040,202 | B2 | 6/2021 | Marnfeldt |
| 11,241,580 | B2 | 2/2022 | Esteller et al. |
| 2012/0092031 | A1 | 4/2012 | Shi et al. |
| 2012/0095519 | A1 | 4/2012 | Parramon et al. |
| 2012/0095529 | A1 | 4/2012 | Parramon et al. |
| 2013/0289665 | A1 | 10/2013 | Marnfeldt et al. |
| 2015/0080982 | A1 | 3/2015 | Funderburk |
| 2015/0157861 | A1 | 6/2015 | Aghassian |
| 2015/0231402 | A1 | 8/2015 | Aghassian |
| 2015/0360038 | A1 | 12/2015 | Zottola et al. |
| 2017/0296823 | A1 | 10/2017 | Hershey et al. |
| 2018/0071520 | A1 | 3/2018 | Weerakoon et al. |
| 2019/0366094 | A1* | 12/2019 | Esteller .................... A61B 5/24 |
| 2021/0252289 | A1 | 8/2021 | Esteller |
| 2022/0062638 | A1 | 3/2022 | Dinsmoor et al. |
| 2022/0184399 | A1 | 6/2022 | Zhang et al. |
| 2022/0266027 | A1 | 8/2022 | Zhang et al. |
| 2022/0296892 | A1 | 9/2022 | Esteller et al. |
| 2023/0248977 | A1 | 8/2023 | Esteller et al. |

OTHER PUBLICATIONS

Miller, Charles A., et al., "Electrically Evoked Compound Action Potentials of Guinea Pig and Cat: Responses to Monopolar, Monophasic Stimulation," Hearing Research, 119, 1998, pp. 142-154.
International Search Report and Written Opinion regarding corresponding PCT Application No. PCT/US2023/072941, mailed Nov. 17, 2023.

* cited by examiner

TEMPLATE BASED ARTIFACT REDUCTION IN NEUROMODULATION APPLICATIONS

CROSS REFERENCE TO RELATED APPLICATIONS

This is a non-provisional of U.S. Provisional Patent Application Ser. No. 63/374,011, filed Aug. 31, 2022, to which priority is claimed, and which is incorporated herein by reference.

FIELD OF THE INVENTION

This application relates to Implantable Medical Devices (IMDs), and more specifically to circuitry to assist with sensing neural responses to stimulation in an implantable stimulator device.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) or Deep Brain Stimulation (DBS) system. However, the present invention may find applicability with any stimulator device system.

A stimulator system typically includes an Implantable Pulse Generator (IPG) 10 shown in FIG. 1. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12, or some conductive portion of the case, can also comprise an electrode (Ec). In an SCS application, the electrode lead(s) are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In a DBS application, the electrode leads are implanted in the brain through holes in the skull, and lead extension are used to connect the leads to the IPG which is typically implanted under the clavicle (collarbone). In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. SCS therapy can relieve symptoms such as chronic back pain, while DBS therapy can alleviate Parkinsonian symptoms such as tremor and rigidity. IPG 10 as described should be understood as including External Trial Stimulators (ETSs), which mimic operation of the IPG 10 during trials periods when leads have been implanted in the patient but the IPG 10 has not. See, e.g., U.S. Pat. No. 9,259,574 (disclosing an ETS).

IPG 10 can include an antenna 27a allowing it to communicate bi-directionally with a number of external devices discussed subsequently. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Zigbee, WiFi, MICS, and the like.

Stimulation in IPG 10 is typically provided by pulses each of which may include a number of phases (30i), as shown in the example of FIG. 2A. Stimulation parameters typically include amplitude (current I, although a voltage amplitude V can also be used); frequency (F); pulse width (PW); the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E1 has been selected as an anode (during its first phase 30a), and thus provides pulses which source a positive current of amplitude +I to the tissue. Electrode E2 has been selected as a cathode (again during first phase 30a), and thus provides pulses which sink a corresponding negative current of amplitude −I from the tissue. This is an example of bipolar stimulation, in which the lead includes one anode pole and one cathode pole. Note that more than one electrode on the lead may be selected to act as an anode electrode to form an anode pole at a given time, and more than one electrode may be selected to act as a cathode to form a cathode pole at a given time, as explained further in U.S. Pat. No. 10,881,859. Stimulation provided by the IPG 10 can also be monopolar. In monopolar stimulation, the lead is programmed with a single pole of a given polarity (e.g., a cathode pole), with the conductive case electrode Ec acting as a return (e.g., an anode pole). Again, more than one electrode on the lead may be active to form the pole during monopolar stimulation.

IPG 10 as mentioned includes stimulation circuitry 28 to form prescribed stimulation at a patient's tissue. FIG. 3 shows an example of stimulation circuitry 28, which includes one or more current source circuits and one or more current sink circuits. The sources and sinks can comprise Digital-to-Analog converters (DACs), and may be referred to as PDACs and NDACs in accordance with the Positive (sourced, anodic) and Negative (sunk, cathodic) currents they respectively issue. In the example shown, a NDACi/PDACi pair is dedicated (hardwired) to a particular electrode node ei 39. Each electrode node ei 39 is associated with an electrode Ei 16 via a DC-blocking capacitor Ci 38, for the reasons explained below. The stimulation circuitry 28 in this example also supports selection of the conductive case 12 as an electrode (Ec 12), which case electrode is typically selected for monopolar stimulation as explained above. PDACs and NDACs can also comprise voltage sources.

Proper control of the PDACs and NDACs allows any of the electrodes 16 to act as anodes or cathodes to create a current through a patient's tissue, R, hopefully with good therapeutic effect. Consistent with the example provided in FIG. 2A, FIG. 3 shows operation during the first phase 30*a* in which electrode E1 has been selected as an anode electrode to source current I to the tissue R and E2 has been selected as a cathode electrode to sink current from the tissue. Thus PDAC1 and NDAC2 are digitally programmed to produce the desired current, I, with the correct timing (e.g., in accordance with the prescribed frequency and pulse widths). As mentioned above, more than one anode electrode and more than one cathode electrode may be selected at one time, and thus current can flow through the tissue R between two or more of the electrodes 16. Other stimulation circuitries 28 can also be used in the IPG 10, including ones that includes switching matrices between the electrode nodes ei 39 and the N/PDACs. See, e.g., 6,181,969, 8,606, 362, 8,620,436, 11,040,192, and 10,912,942. Much of the stimulation circuitry 28 of FIG. 3, including the PDACs and NDACs, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519. As explained in these references, ASIC(s) may also contain other circuitry useful in the IPG 10, such as IPG master control circuitry 102 (see FIG. 5), telemetry circuitry (for interfacing off chip with telemetry antennas 27*a* and/or 27*b*), circuitry for generating the compliance voltage VH (as explained next), various measurement circuits, etc.

Power for the stimulation circuitry 28 is provided by a compliance voltage VH, as described in further detail in U.S. Patent Application Publications 2013/0289665 and 2018/0071520. The compliance voltage VH may be coupled to the source circuitry (e.g., the PDAC(s)), while ground may be coupled to the sink circuitry (e.g., the NDAC(s)), such that the stimulation circuitry 28 is powered by VH and ground. Other power supply voltages may be used with the PDACs and NDACs, and explained in U.S. Patent Application Publication 2018/0071520, but these aren't shown in FIG. 3 for simplicity.

Preferably, and as described in U.S. Pat. No. 11,040,202, the compliance voltage VH can be produced by a VH regulator 49. VH regulator 49 receives the voltage of the battery 14 (Vbat) and boost this voltage to a higher value required for the compliance voltage VH. VH regulator 49 can comprise an inductor-based boost converter or a capacitor-based charge pump for example. The regulator 49 can vary the value of VH based on measurements taken from the stimulation circuitry 28. As explained in detail in the '202 patent, VH measurement circuitry 51 can be used to measure the voltage drops across the active DACs (e.g., PDAC1 (Vp1) and NDAC2 (Vn2) in the example shown in FIG. 3) in the stimulation circuitry 28. Using such measurements allows VH to be established at an energy-efficient level: high enough to form the prescribed current without loading (i.e., without producing less current that prescribed), yet low enough to not needlessly waste power in the stimulation circuitry 28 when forming the prescribed current. In this respect, VH can be variable, and typically ranges from about 5 to 15 Volts.

The VH measurement circuitry 51 can output an enable signal VH(en1) indicating when VH regulator 49 should increase the level of VH, i.e., when the voltage drops across the active DACs are too low. This enable signal VH(en1) may be processed at logic 53 in conjunction with other signals explained below to determine a master enable signal VH(en) for the VH regulator 49. Logic 53 may be associated with the IPG's control circuitry 102. Master enable signal VH(en) when asserted causes the VH regulator 49 to increase VH (e.g., when the current starts to load). Deasserting VH(en) disable the VH regulator, which allows VH to naturally decrease over time until it needs to be increased again. This feedback generally causes VH to be established at an energy-efficient value appropriate for the current that is being provided by the stimulation circuitry 28.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861. While useful, DC-blocking capacitors 38 are not strictly required in all IPG designs and applications.

Referring again to FIG. 2A, the stimulation pulses as shown are biphasic, with each pulse comprising a first phase 30*a* followed thereafter by a second phase 30*b* of opposite polarity. Biphasic pulses are useful to actively recover any charge that might be stored on capacitive elements in the electrode current paths, such as on the DC-blocking capacitors 38. Charge recovery is shown with reference to both FIGS. 2A and 2B. During the first pulse phase 30*a*, charge will (primarily) build up across the DC-blockings capacitors C1 and C2 associated with the electrodes E1 and E2 used to produce the current, giving rise to voltages Vc1 and Vc2 (I=C*dV/dt). During the second pulse phase 30*b*, when the polarity of the current I is reversed at the selected electrodes E1 and E2, the stored charge on capacitors C1 and C2 is recovered, and thus voltages Vc1 and Vc2 hopefully return to 0 V at the end the second pulse phase 30*b*.

Charge recovery using phases 30*a* and 30*b* is said to be "active" because the P/NDACs in stimulation circuitry 28 actively drive a current, in particular during the last phase 30*b* to recover charge stored after the first phase 30*a*. However, such active charge recovery may not be perfect, and some residual charge may be present in capacitive structures even after phase 30*b* is completed. Accordingly, the stimulation circuitry 28 can also provide for passive charge recovery. Passive charge recovery is implemented using passive charge recovery switches PRi 41 as shown in FIG. 3. These switches 41 when selected via assertion of control signals <Xi> couple each electrode node ei to a passive recovery voltage Vpr established on bus 43. As explained in USPs 10,716,937 and 10,792,491, this allows any stored charge to be recovered through the patient's tissue, R. Control signals <Xi> are usually asserted to cause passive charge recovery after each pulse (e.g., after each last phase 30*b*) during periods 30*c* shown in FIG. 2A. Because passive charge recovery involves capacitive discharge through the resistance R of the patient's tissue, such discharge manifests as an exponential decay in current, as shown in FIG. 2A. As also discussed in the '937 patent, each of the passive charge recovery switches 41 can be associated with a variable resistance, and as such each switch 41 can be controlled by a bus of signals <Xi> to control the resistance at which passive charge recovery occurs—i.e., the on resistance of the switches 41 when they are closed. Passive charge recovery during period 30*c* may be followed by a quiet period 30*d* during which no active current is driven by the DAC circuitry, and none of the passive recovery switches 41 are closed. This quiet period 30*d* may last until the next pulse is actively produced (e.g., phase 30*a*). Like the particulars of pulse phases 30*a* and 30*b*, the occurrence of passive charge recovery (30*c*) and any quiet periods (30*d*) can be prescribed as part of the stimulation program.

FIG. 4 shows various external systems 60, 70, and 80 that can wirelessly communicate data with the IPG 10. Such systems can be used to wirelessly transmit a stimulation program to the IPG 10—that is, to program its stimulation circuitry 28 to produce stimulation with desired amplitudes and timings as described earlier. Such systems may also be used to adjust one or more stimulation parameters of a stimulation program that the IPG 10 is currently executing, and/or to wirelessly receive information from the IPG 10, such as various status information, etc.

External controller 60 can be as described in U.S. Patent Application Publication 2015/0080982 for example, and may comprise a portable, hand-held controller dedicated to work with the IPG 10. External controller 60 may also comprise a general-purpose mobile electronics device such as a mobile phone which has been programmed with a Medical Device Application (MDA) allowing it to work as a wireless controller for the IPG 10, as described in U.S. Patent Application Publication 2015/0231402. External controller 60 includes a display 61 and a means for entering commands, such as buttons 62 or selectable graphical icons provided on the display 61. The external controller 60's user interface enables a patient to adjust stimulation parameters, although it may have limited functionality when compared to systems 70 and 80, described shortly. The external controller 60 can have one or more antennas capable of communicating with the IPG 10. For example, the external controller 60 can have a near-field magnetic-induction coil antenna 64*a* capable of wirelessly communicating with the coil antenna 27*a* in the IPG 10. The external controller 60 can also have a far-field RF antenna 64*b* capable of wirelessly communicating with the RF antenna 27*b* in the IPG 10.

Clinician programmer 70 is described further in U.S. Patent Application Publication 2015/0360038, and can comprise a computing device such as a desktop, laptop, or notebook computer, a tablet, a mobile smart phone, a Personal Data Assistant (PDA)-type mobile computing device, etc. In FIG. 4, the computing device is shown as a laptop computer that includes typical computer user interface means such as a display 71, buttons 72, as well as other user-interface devices such as a mouse, a keyboard, speakers, a stylus, a printer, etc., not all of which are shown for convenience. Also shown in FIG. 4 are accessory devices for the clinician programmer 70 that are usually specific to its operation as a stimulation controller, such as a communication "wand" 76 coupleable to suitable ports on the computing device. The antenna used in the clinician programmer 70 to communicate with the IPG 10 can depend on the type of antennas included in the IPG 10. If the patient's IPG 10 includes a coil antenna 27*a*, wand 76 can likewise include a coil antenna 74*a* to establish near-field magnetic-induction communications at small distances. In this instance, the wand 76 may be affixed in close proximity to the patient, such as by placing the wand 76 in a belt or holster wearable by the patient and proximate to the patient's IPG 10. If the IPG 10 includes an RF antenna 27*b*, the wand 76, the computing device, or both, can likewise include an RF antenna 74*b* to establish communication with the IPG 10 at larger distances. The clinician programmer 70 can also communicate with other devices and networks, such as the Internet, either wirelessly or via a wired link provided at an Ethernet or network port.

External system 80 comprises another means of communicating with and controlling the IPG 10 via a network 85 which can include the Internet. The network 85 can include a server 86 programmed with communication and control functionality, and may include other communication networks or links such as WiFi, cellular or land-line phone links, etc. The network 85 ultimately connects to an intermediary device 82 having antennas suitable for communication with the IPG's antenna, such as a near-field magnetic-induction coil antenna 84*a* and/or a far-field RF antenna 84*b*. Intermediary device 82 may be located generally proximate to the IPG 10. Network 85 can be accessed by any user terminal 87, which typically comprises a computer device associated with a display 88. External system 80 allows a remote user at terminal 87 to communicate with and control the IPG 10 via the intermediary device 82.

FIG. 4 also shows circuitry 90 involved in any of external systems 60, 70, or 80. Such circuitry can include control circuitry 92, which can comprise any number of devices such as one or more microprocessors, microcomputers, FPGAs, DSPs, other digital logic structures, etc., which are capable of executing programs in a computing device. Such control circuitry 92 may contain or coupled with memory 94 which can store external system software 96 for controlling and communicating with the IPG 10, and for rendering a Graphical User Interface (GUI) 99 on a display (61, 71, 88) associated with the external system. In external system 80, the external system software 96 would likely reside in the server 86, while the control circuitry 92 could be present in either or both the server 86 or the terminal 87.

SUMMARY

Disclose herein is a system for providing electrical stimulation to a patient's spinal cord using one or more electrode leads implantable in the patient's spinal column, each electrode lead comprising a plurality of spinal electrode contacts, the system comprising: a neurostimulator that is connectable to the one or more electrode leads, and control circuitry configured to: cause the neurostimulator to use one or more of the spinal electrode contacts to provide a first electrical stimulation to the patient's spinal cord, wherein the first electrical stimulation is configured to evoke a first stimulation artifact but not to evoke a detectable neural response in the patient's spinal cord, cause the neurostimulator to use a second one or more of the spinal electrode contacts to record a first signal comprising a first stimulation artifact component, fit the first signal to a mathematical model to yield a template signal, cause the neurostimulator to use one or more of the spinal electrode contacts to provide second electrical stimulation to the patient's spinal cord, wherein the second electrical stimulation is configured to evoke a second stimulation artifact and a neural response in the patient's spinal cord, cause the neurostimulator to use a one or more of the spinal electrode contacts to record a second signal comprising a second stimulation artifact component and a neural response component, and use the second signal and the template signal to determine a third signal, wherein the third signal comprises the neural response component and comprises a smaller stimulation artifact component than does the second signal. According to some embodiments, the amplitude of the first electrical stimulation is less than the amplitude of the second electrical stimulation. According to some embodiments, the mathematical model comprises an exponential decay. According to some embodiments, using the second signal and the template to determine a third signal comprises scaling the template signal with respect to the second signal. According to some embodiments, using the second signal and the template to determine a third signal comprises subtracting the scaled template signal from the second signal to yield the third signal. According to some embodiments, the control circuitry is control circuitry of the neurostimulator. According to some embodiments, the control circuitry is control circuitry of an external computing device. According to some embodiments, the control circuitry is further configured to display a representation of the third signal on a graphical display of the external computing device. According to some embodiments, the control circuitry is further configured to determine one or more features of the third signal. According to some embodiments, the control circuitry is configured to use the one or more features for closed loop feedback adjustment of therapeutic stimulation. According to some embodiments, the therapeutic stimulation is the second electrical stimulation. According to some embodiments, the closed loop feedback adjustment is configured to maintain the therapeutic stimulation within a therapeutic window. According to some embodiments, the mathematical model comprises a term of the form $$V(t) = V_0 e^{\frac{-t}{\tau}},$$

where V(t) is voltage as a function of time t, V0 is peak voltage, and $\tau$ is a decay time constant. According to some embodiments, the decay time constant $\tau$ depends on the resistance R and capacitance C of tissue near the electrode contacts. According to some embodiments, the neural response is a compound evoked action potential (ECAP).

Also disclosed herein is a method for providing electrical stimulation to a patient's spinal cord using one or more electrode leads implantable in the patient's spinal column, each electrode lead comprising a plurality of spinal electrode contacts, the method comprising: using one or more of the spinal electrode contacts to provide a first electrical stimulation to the patient's spinal cord, wherein the first electrical stimulation is configured to evoke a first stimulation artifact but not to evoke a detectable neural response in the patient's spinal cord, using a second one or more of the spinal electrode contacts to record a first signal comprising a first stimulation artifact component, fitting the first signal to a mathematical model to yield a template signal, using one or more of the spinal electrode contacts to provide second electrical stimulation to the patient's spinal cord, wherein the second electrical stimulation is configured to evoke a second stimulation artifact and a neural response in the patient's spinal cord, using a one or more of the spinal electrode contacts to record a second signal comprising a second stimulation artifact component and a neural response component, and using the second signal and the template signal to determine a third signal, wherein the third signal comprises the neural response component and comprises a smaller stimulation artifact component than does the second signal. According to some embodiments, the amplitude of the first electrical stimulation is less than the amplitude of the second electrical stimulation. According to some embodiments, the mathematical model comprises an exponential decay. According to some embodiments, using the second signal and the template to determine a third signal comprises scaling the template signal with respect to the second signal. According to some embodiments, the second signal and the template to determine a third signal comprises subtracting the scaled template signal from the second signal to yield the third signal. According to some embodiments, the control circuitry is control circuitry of the neurostimulator. According to some embodiments, the control circuitry is control circuitry of an external computing device. According to some embodiments, the control circuitry is further configured to display a representation of the third signal on a graphical display of the external computing device. According to some embodiments, the control circuitry is further configured to determine one or more features of the third signal. According to some embodiments, the control circuitry is configured to use the one or more features for closed loop feedback adjustment of therapeutic stimulation. According to some embodiments, the therapeutic stimulation is the second electrical stimulation. According to some embodiments, the closed loop feedback adjustment is configured to maintain the therapeutic stimulation within a therapeutic window. According to some embodiments, the mathematical model comprises a term of the form $$V(t) = V_0 e^{\frac{-t}{\tau}},$$

where V(t) is voltage as a function of time t, V0 is peak voltage, and $\tau$ is a decay time constant. According to some embodiments, the decay time constant $\tau$ depends on the resistance R and capacitance C of tissue near the electrode contacts. According to some embodiments, the neural response is a compound evoked action potential (ECAP).

The invention may also reside in the form of a programed external device (via its control circuitry) for carrying out the above methods, a programmed IPG or ETS (via its control circuitry) for carrying out the above methods, a system including a programmed external device and IPG or ETS for carrying out the above methods, or as a computer readable media for carrying out the above methods stored in an external device or IPG or ETS.

DETAILED DESCRIPTION

An increasingly interesting development in pulse generator systems is the addition the capability to sense electric potentials in the patient's tissue to complement the stimulation that such systems provide. For example, and as explained in U.S. Patent Application Publication 2017/0296823, it can be beneficial to sense a neural response produced by neural tissue that has received stimulation from an IPG. U.S. Patent Application Publication 2017/0296823 shows an example where sensing of neural responses is useful in an SCS context, and in particular discusses the sensing of Evoked Compound Action Potentials, or "ECAPs." U.S. Pat. No. 10,940,316 describes methods and systems capable of adjusting stimulation when a patient changes postures based on measurements of neural responses. U.S. Patent Application Publication 2022/0184399 describes methods and systems for using recorded neural responses to sense movement of an electrode array during SCS and to adjust stimulation accordingly.

Figure 5:
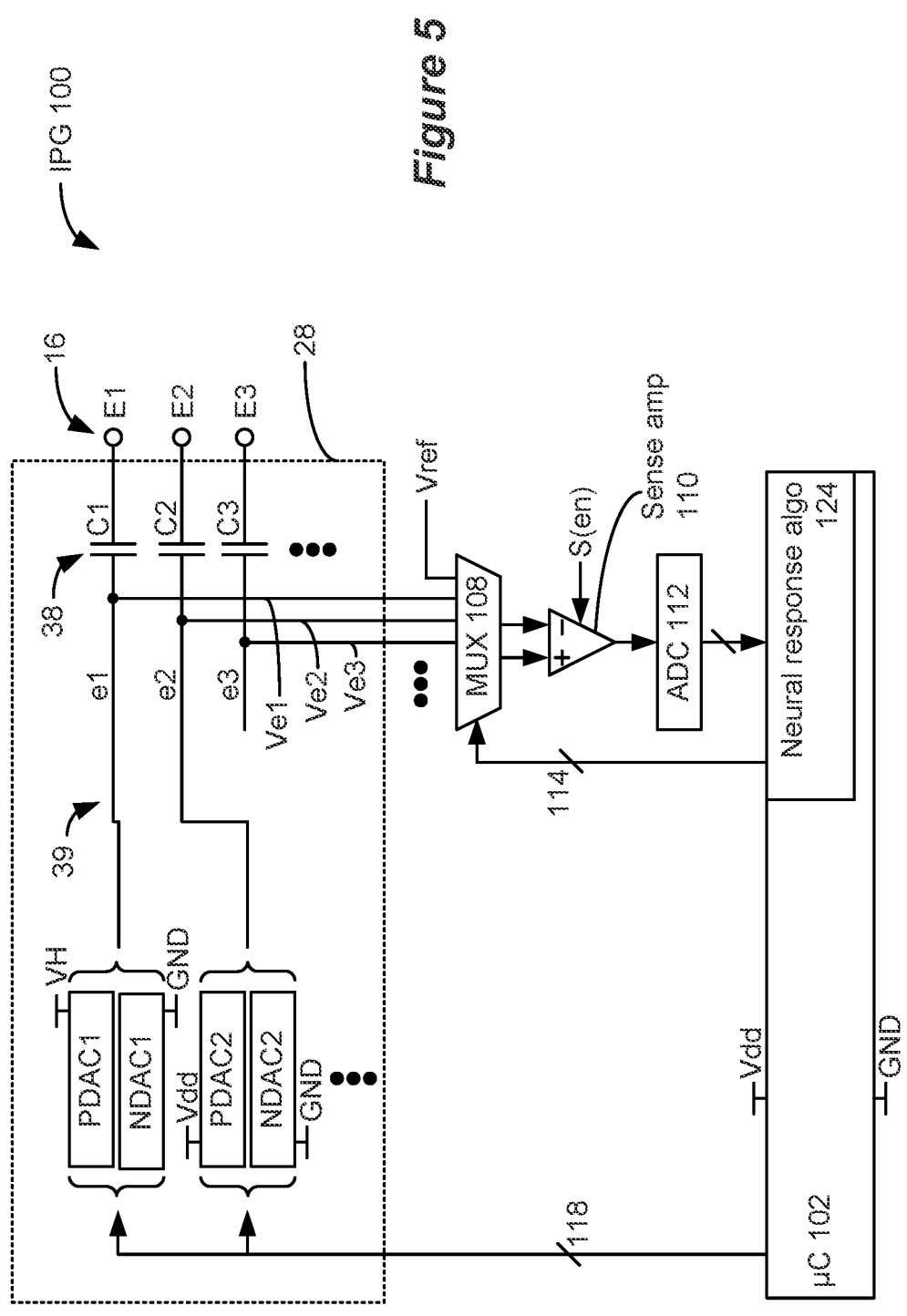
FIG. 5 shows a IPG having neural response sensing capability.

FIG. 5 shows basic circuitry for sensing neural responses in an IPG 100. The IPG 100 includes control circuitry 102, which may comprise a microcontroller for example, such as Part Number MSP430, manufactured by Texas Instruments, which is described in data sheets accessible on the Internet. Other types of control circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs) in the IPG 10 as described earlier, which ASIC(s) may additionally include the other circuitry shown in FIG. 5.

Figures 1, 2A, 2B:
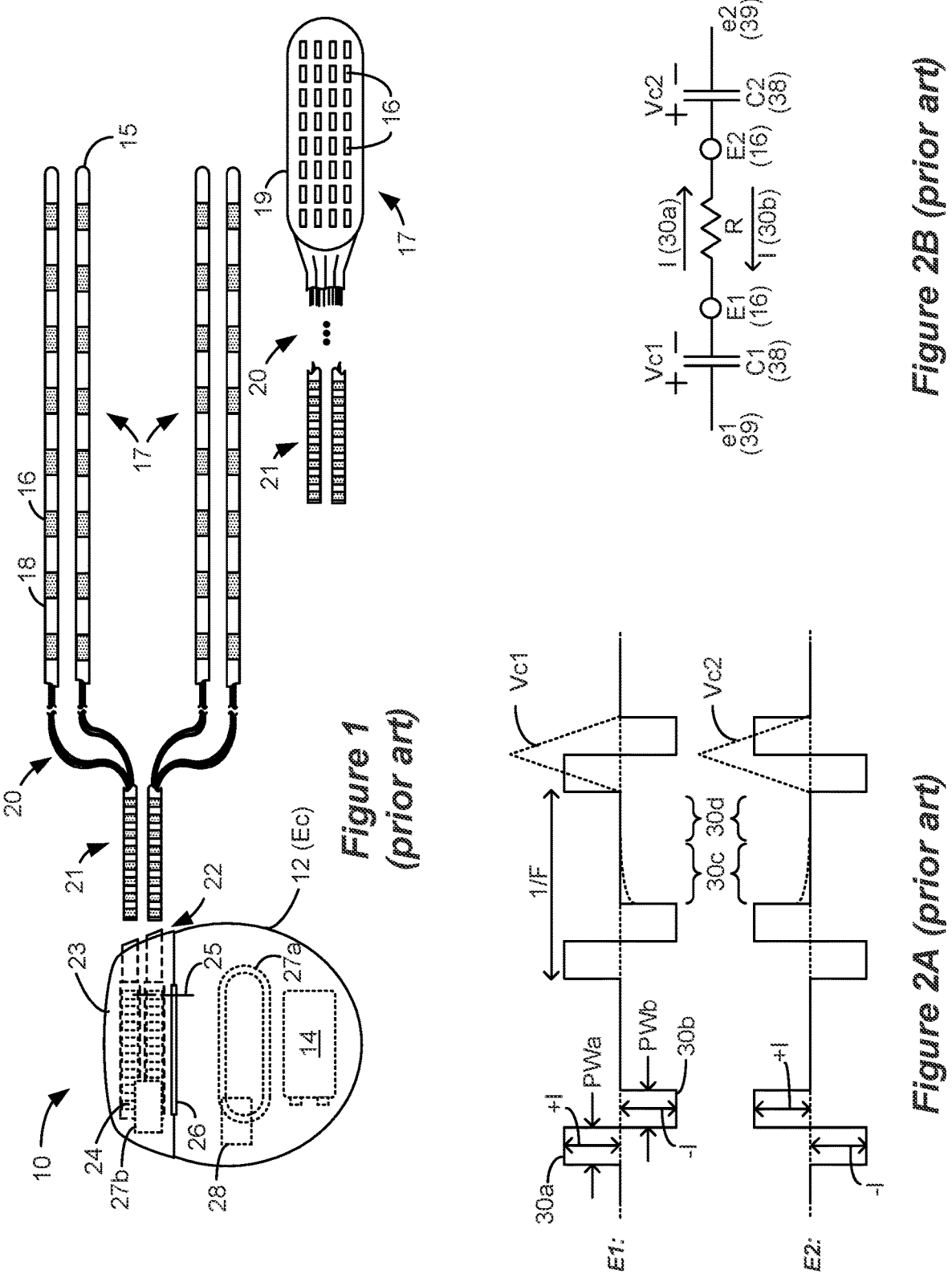
FIG. 1 shows an Implantable Pulse Generator (IPG), in accordance with the prior art.
FIGS. 2A and 2B show an example of stimulation pulses producible by the IPG, in accordance with the prior art.
Figure 3:
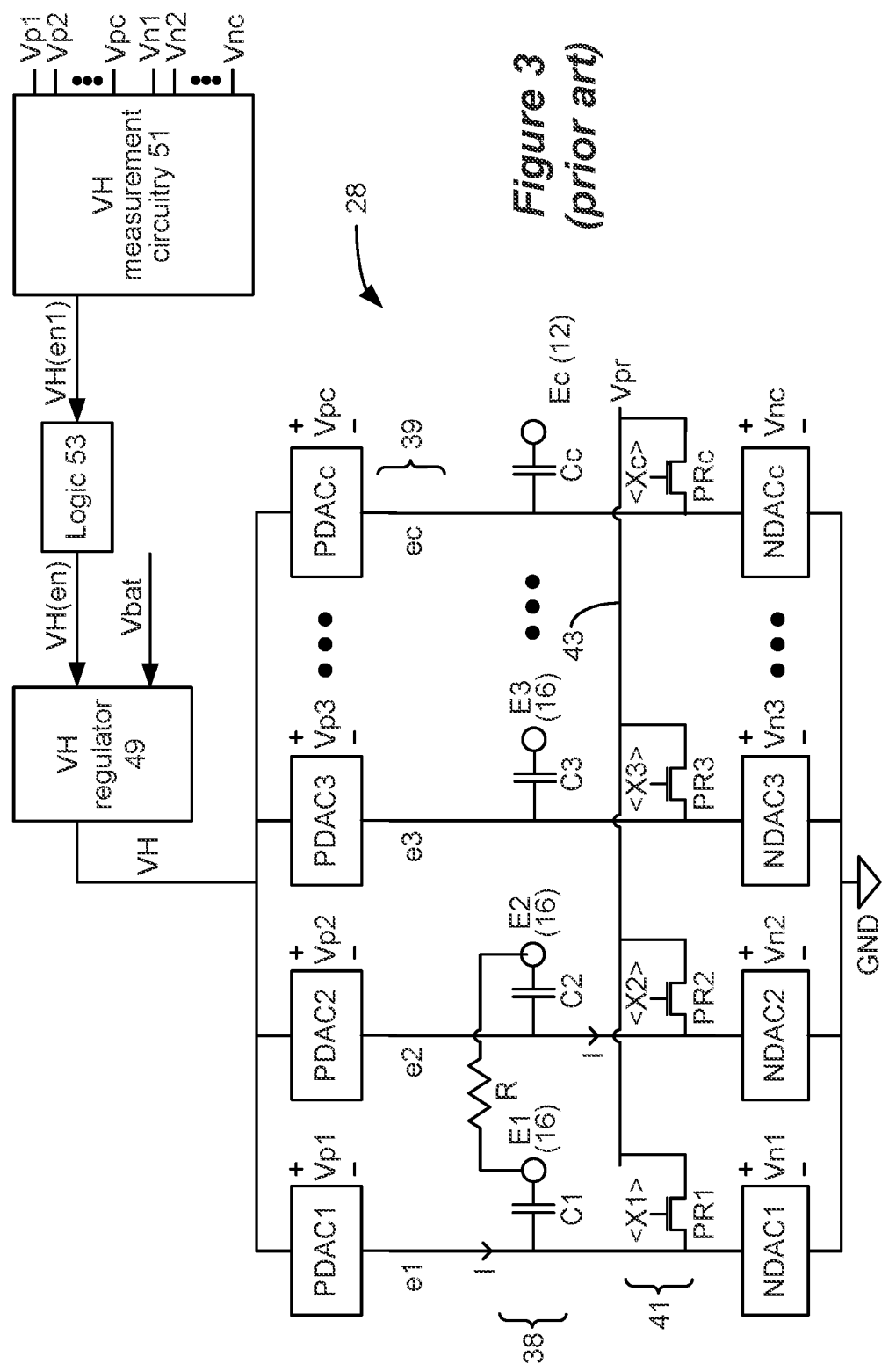
FIG. 3 shows stimulation circuitry useable in the IPG, in accordance with the prior art.

FIG. 5 includes the stimulation circuitry 28 described earlier (FIG. 3), including one or more DACs (PDACs and NDACs). A bus 118 provides digital control signals to the DACs to produce currents or voltages of prescribed amplitudes and with the correct timing at the electrodes selected for stimulation. The electrode current paths to the electrodes 16 include the DC-blocking capacitors 38 described earlier.

Figure 4:
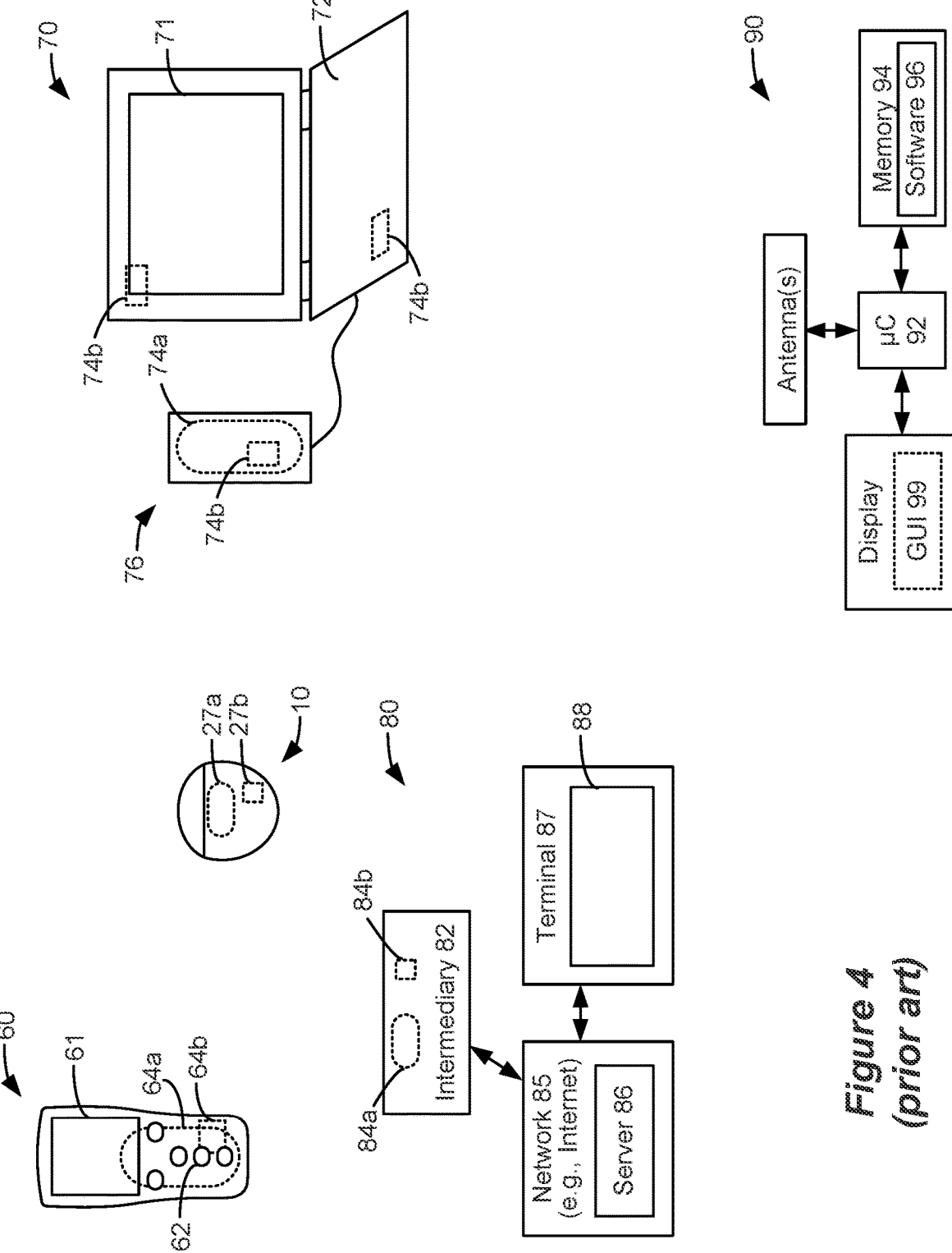
FIG. 4 shows various external devices capable of communicating with and programming stimulation in an IPG, in accordance with the prior art.

FIG. 5 also shows circuitry used to sense neural responses. As shown, the electrode nodes 39 are input to a multiplexer (MUX) 108. The MUX 108 is controlled by a bus 114, which operates to select one or more electrode nodes, and hence to designate corresponding electrodes 16 as sensing electrodes. The sensing electrode(s) selected via bus 114 can be determined automatically by control circuitry 102 and/or a neural response algorithm 124, as described further below. However, the sensing electrode(s) may also be selected by the user (e.g., a clinician) via an external system 60, 70 or 80 (FIG. 4).

The analog waveform comprising the sensed neural response and output by the sense amp circuitry 110 is preferably converted to digital signals by an Analog-to-Digital converter (ADC) 112, and input to the IPG's control circuitry 102. The ADC 112 can be included within the control circuitry 102's input stage as well. The control circuitry 102 can be programmed with a neural response algorithm 124 to evaluate the neural responses, and to take appropriate actions as a result. For example, the neural response algorithm 124 may change the stimulation in accordance with the sensed neural response, and can issue new control signals via bus 118 to change operation of the stimulation circuitry 28 to affect better treatment for the patient. As explained in more detail below, one or more algorithms may be configured to extract (calculate) values for features of the neural response (such as peak heights, curve areas, etc.) and to use those calculated values as indications of efficacy, for closed-loop adjustment of stimulation, and the like.

Neural responses to stimulation are typically small-amplitude AC signals on the order of microVolts or milliVolts, which can make sensing difficult. The sense amp circuitry 110 needs to be capable of resolving this small signal, and this is particularly difficult when one realizes that this small signal typically rides on a background voltage otherwise present in the tissue. The background voltage can be caused by the stimulation itself. In particular, stimulation can give rise to a "stimulation artifact," which is results from electromagnetic fields arising the patient's tissue. The stimulus artifact waveform may be several orders of magnitude greater than the ECAP and typically decays with a time constant of several hundreds of microseconds, which is sufficiently long to overlap with the ECAP response. Both the stimulation artifact and the ECAP propagate rostrally and caudally from the location of the stimulating electrodes. The propagation speed of the two signals are typically different; typically, the stimulation artifact propagates faster. So, the stimulation artifact and the ECAP signal may overlap to different degrees, depending on which electrodes are used to record the signals. The overlap of the stimulation artifact with the ECAP makes it difficult to calculate values for the various features of ECAP, as explained below.

Figure 6:
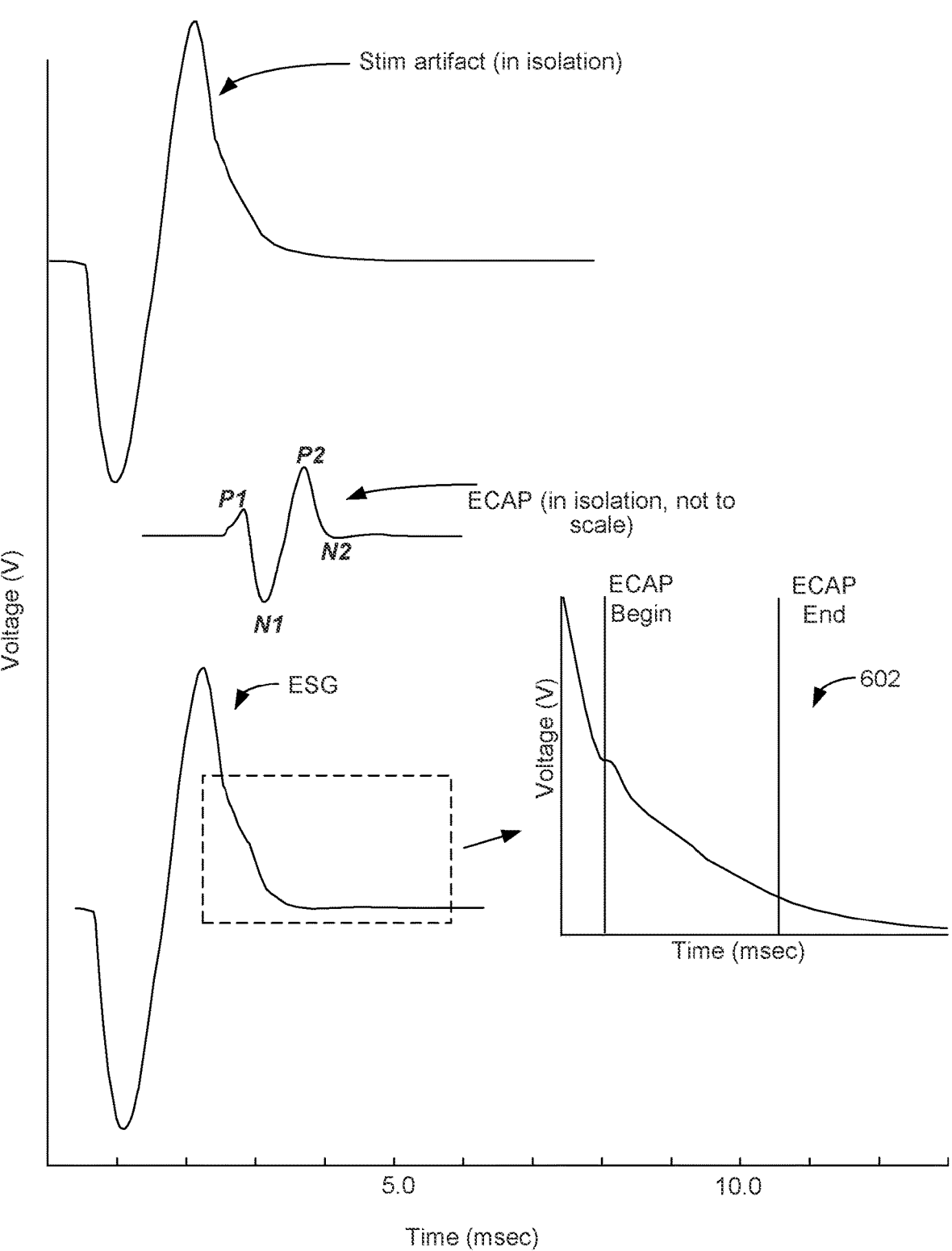
FIG. 6 shows a stimulation artifact and an ECAP, each in isolation, as well as both signals combined in an ESG.

FIG. 6 illustrates a recorded stimulation artifact and ECAP each in isolation, as well as an electrospinagram (ESG) that contains each of the recorded signals. An ECAP comprises a cumulative response provided by neural fibers that are recruited by the stimulation, and essentially comprises the sum of the action potentials of recruited neural elements (ganglia or fibers) when they "fire." The ECAP comprises a number of peaks that are conventionally labeled with P for positive peaks and N for negative peaks, with P1 comprising a first positive peak, N1 a first negative peak, P2 a second positive peak, N2 a second negative peak, and so on. Note that not all ECAPs will have the exact shape and number of peaks as illustrated in FIG. 6, because an ECAP's shape is a function of the number and types of neural elements that are recruited and that are involved in its conduction. Also note that the isolated ECAP and the isolated artifact signals are not drawn to scale. As explained above, the artifact signal is typically orders of magnitude larger than the ECAP signal. Accordingly, as shown in the combined ESG, it may be difficult to discern the ECAP signal if it overlaps the artifact signal.

Various forms of artifact reduction techniques have been described in the literature. Two common techniques are the forward masking method and the alternating polarity method. Both techniques are well described in the art. See, e.g., Akhoun, et al., *Electrically evoked compound action potential artifact rejection by independent component analysis: Technique validation, Hear. Res.* 302:60-73, (2013).

Briefly, the forward masking method involves issuing a masking pulse, which sets the neural elements in a refractory state. Then a probe pulse is issued, which allows measuring the resulting artifact (the probe artifact), absent any neural response. During subsequent measurements, the neural signal can be determined by subtracting the determined probe artifact from the overall signal, ideally leaving only the neural response (i.e., the ECAP).

The alternating polarity requires two buffers to be recorded and summed together: one buffer resulting from a cathodic-first pulse and the other resulting from an anodic-first pulse. It is assumed that the artifacts resulting from the two pulses cancel and that the neural responses add together, yielding an ECAP with double the amplitude in the summed signal.

Both the forward masking method and the alternating polarity method rely upon assumptions that are known to be only approximately true. For example, the forward masking method assumes that all the neural elements are in a refractory state when the probe stimulus is issued. However, neural elements that are not in a refractory state when the probe stimulus is issued results in the probe "artifact" signal including some contribution from neural responses, which neural responses are subsequently subtracted from resulting ECAP measurement, yielding an inaccurate ECAP measurement. Likewise, in the alternating polarity method, the cathodic-first pulse and the anodic-first pulse may not generate the same neural activity; the ECAPs may have different latencies and amplitudes, resulting in distorted ECAPs when the two ECAPs are summed together. Likewise, the assumption that the stimulation artifacts for the two polarities are equal and opposite may not hold in all cases. U.S. Pat. No. 11,241,580, issued Feb. 8, 2022, the contents of which are incorporated herein by reference, discloses template subtraction methods of artifact reduction that overcome some of the problems associated with the techniques described above.

The inventors have determined new template-based methods for reducing or removing stimulation artifact interference from neural responses recorded using spinal electrodes, as described above. Specifically, the techniques and algorithms described herein are useful when the neural artifact is overlapped by the decaying residual charge portion 602 of the stimulation artifact, as shown in FIG. 6.

Figures 7, 8:
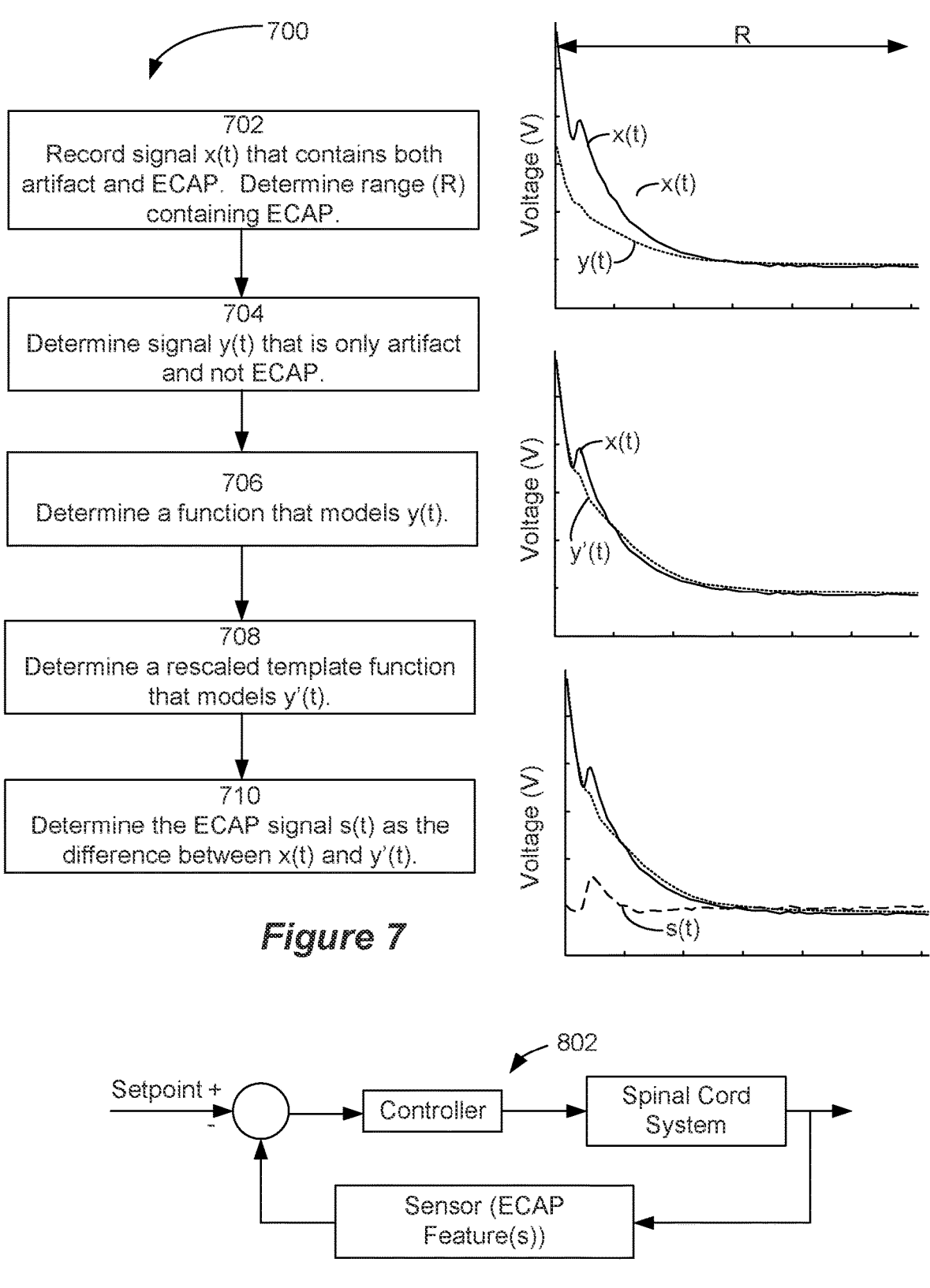
FIG. 7 shows an algorithm for reducing a stimulation artifact.
FIG. 8 shows a closed-loop feedback controller.

FIG. 7 illustrates one embodiment of an algorithm 700 for removing a stimulation artifact signal from a recorded neural response (such as an ECAP). Step 702 involves applying stimulation at stimulating electrodes that is configured to evoke an ECAP and recording a signal at recording electrodes that contains both a stimulation artifact and an ECAP signal. The recorded signal x(t) may be analyzed to determine the range (R) of times at which the ECAP is present within the artifact signal. For example, the inset signal 602 (FIG. 6) contains both ECAP and stimulation artifact contributions. The range at which the ECAP is present in such a signal may be determined. According to some embodiments, particularly when the algorithm 700 is conducted in a clinical setting and the resulting recorded signals are displayed on a user interface, a person (e.g., a clinician) may simply observe the signal and try to discern peaks and/or troughs associated with the P1, N1, P2, etc. features of the ECAP within the signal x(t). According to some embodiments, the clinician may compare recording channels to confirm the identification of ECAP features within the x(t) signal, i.e., because on different channels the ECAP features will be separated differently from the artifact signal because of differences in propagation rates, as explained above. In other embodiments, peak detection algorithms or the like may be used to determine a range at which an ECAP is present in the signal x(t). FIG. 7 shows a range (R) of a signal x(t) that contains both artifact and ECAP.

Step 704 involves determining (over the range R) a signal y(t) that does not contain any ECAP contribution. For example, this may involve applying stimulation using the stimulating electrodes wherein the stimulation does not sufficient intensity to evoke an ECAP. In other words, the y(t) corresponds to "sub-threshold" stimulation, i.e., stimulation that is below the intensity threshold required to evoke a detectable ECAP. FIG. 7 illustrates an artifact signal y(t) over the range R.

Step 706 involves determining a function that models the subthreshold signal y(t). According to some embodiments, the residual charge decay of the stimulation artifact can be modeled as a voltage decay of an RC circuit, according to equation (EQ1):

$$V(t) = V_0 e^{\frac{-t}{\tau}} \qquad \text{EQ1}$$

where $V_0$ is the peak (or max) voltage and $\tau$ is a decay time constant determined by the resistance R and capacitance C of the tissue near the electrodes. An exponential decay, as depicted by EQ 1, is one example of a function that models the residual artifact term within the subthreshold signal y(t). Other functions, such as polynomial functions, spline functions, or the like may be used, according to some embodiments. Alternatively, a bandpass/high pass filter may perform an equivalent operation/removal of the artifact. According to some embodiments, a bandpass filter that matches the RC decay using an optimization (least-squares, for example) may be used.

If the residual decay of the stimulation artifact is modeled according to equation EQ1, the function x(t), which includes both the residual stimulation artifact and the ECAP signal, may be represented by the equation EQ 2:

$$x(t) = s(t) + V_{01} e^{\frac{-t}{\tau}} + n(t) \qquad \text{EQ2}$$

where s(t) is the ECAP signal in isolation, $V_{01}$ is the peak voltage of the signal that contains the ECAP, and n(t) is noise. Likewise, the subthreshold signal function y(t) may be given as equation EQ 3:

$$y(t) = V_{02} e^{\frac{-t}{\tau}} + n(t) \qquad \text{EQ3}$$

where $V_{01}$ is the peak voltage of the subthreshold signal (and is typically smaller than $V_{01}$).

Step 708 involves using the y(t) function to determine a rescaled function y'(t) that can be used as a template to subtract from the combined function x(t) to yield the ECAP signal in isolation (s(t)). Since it can typically be assumed that the R and C values of the tissue do not change, any two residual artifact signals determined at different stimulation currents should differ only with respect to their $V_0$ values. Moreover, the $V_0$ values typically depend linearly on the stimulation amplitude. Accordingly, y'(t) may be expressed according to equation EQ4:

$$y'(t) = \frac{\max(x(t))}{\max(y(t))} y(t) \approx V_{01} e^{\frac{-t}{\tau}} + n(t) \qquad \text{EQ4}$$

Step 710 involves determining the signal s(t) that represents only the ECAP. Once y'(t) is determined, then the s(t) can be determined by subtracting y'(t) from the combined function x(t), as shown in equation EQ5:

$$s(t)=x(t)-y'(t) \hspace{3cm} \text{EQ5}$$

The signal s(t), which represents the neural response (e.g., the ECAP) and in which the stimulation artifact is reduced or absent, can be used in any of the applications described above. According to some embodiments, the algorithm 700 may be executed in part or in whole on an external computing device, such as a clinician programmer 70 (FIG. 4). Such embodiments may be particularly applicable within a clinical environment. For example, the clinician may wish to record and visualize neural responses (such as ECAPs). In such embodiments, the algorithm may be configured within the external computing device and may perform either manual or automatic neural response detection. The algorithm may guide the user through the steps of collecting data with and without neural responses (i.e., y(t) and x(t) measurements, as described above). The algorithm may then perform the calculations described above and display the signal s(t), which represents the neural response (e.g., the ECAP) and in which the stimulation artifact is reduced or absent, on the screen of the external computing device.

According to some embodiments, the disclosed algorithms, such as algorithm 700, may be embodied in control circuitry of an IPG, for example, as part of the neural response algorithm 124 (FIG. 5). Such embodiments are particularly relevant for allowing the IPG to use features determined from the recorded neural responses to adjust stimulation parameters of the IPG. In such an embodiment, the algorithm may periodically cause the IPG to provide sub-threshold stimulation and supra-threshold stimulation and to collect the signals y(t) and x(t), respectively. Thus, the template signal y'(t) can be periodically calculated and stored in the IPG. To perform closed-loop control, the algorithm may subtract the stored template signal y'(t) from signals recorded in response to the therapeutic stimulation provided by the IPG, thereby yielding the s(t) signal, which comprises the neural response with reduced or absent stimulation artifact. Or, as mentioned above, the algorithm may use a FIR filter (e.g. bandpass or high pass) that performs an approximation of the template removal on the artifact residual, thereby yielding s(t). The neural response algorithm may then extract one or more features of the reduced-artifact signal s(t). For example, the algorithm can determine one or more neural response features (e.g., ECAP features), which may include but are not limited to:

a height of any peak (e.g., N1);

a peak-to-peak height between any two peaks (such as from N1 to P2);

a ratio of peak heights (e.g., N1/P2);

a peak width of any peak (e.g., the full-width half-maximum of N1);

an area or energy under any peak;

a total area or energy comprising the area or energy under positive peaks with the area or energy under negative peaks subtracted or added;

a length of any portion of the curve of the ECAP (e.g., the length of the curve from P1 to N2);

any time defining the duration of at least a portion of the ECAP (e.g., the time from P1 to N2);

a time delay from stimulation to issuance of the ECAP, which is indicative of the neural conduction speed of the ECAP, which can be different in different types of neural tissues;

a conduction speed (i.e., conduction velocity) of the ECAP, which can be determined by sensing the ECAP as it moves past different sensing electrodes;

a rate of variation of any of the previous features, i.e., how such features change over time;

a power (or energy) determined in a specified frequency band (e.g., delta, alpha, beta, gamma, etc.) determined in a specified time window (for example, a time window that overlaps the neural response, the stimulation artifact, etc.);

any mathematical combination or function of these variables;

Such ECAP features may be approximated by the feature extraction algorithm. For example, the area under the curve may comprise a sum of the absolute value of the sensed digital samples over a specified time interval. Similarly, curve length may comprise the sum of the absolute value of the difference of consecutive sensed digital samples over a specified time interval. ECAP features may also be determined within particular time intervals, which intervals may be referenced to the start of simulation, or referenced from within the ECAP signal itself (e.g., referenced to peak N1 for example).

Once the feature extraction algorithm 140 determines one or more of these features, it may then be used to any useful effect in the IPG 100, and specifically may be used to adjust the stimulation that the IPG 100 provides, for example by providing new data to the stimulation circuitry 28 via bus 118. This is explained further in some of the U.S. patent documents cited above. For example, if the distance between the stimulation electrode(s) and the patient's spinal cord changes (for example, because of postural changes, coughing, movement, etc.), the stimulation may be adjusted based on the extracted features to maintain optimum therapeutic stimulation.

The IPG may comprise a closed loop feedback control algorithm that is configured to use the one or more neural response feature values as control variables. Closed-loop feedback control is well known in the art and is not discussed here in detail, but the control scheme may involve controllers such PID controllers, Kalman filters, or the like. FIG. 8 illustrates a simplified control diagram 802, whereby a controller (e.g., IPG control circuitry) controls stimulation based on the ECAP feature(s) determined based on the recorded responses that have been processed to remove or reduce the stimulation artifact, as described above. The feedback control algorithm may adjust stimulation parameters to seek to maintain the sensed ECAP features with respect to a setpoint, threshold, range, etc., for example. According to some embodiments, the feedback control algorithm is configured to maintain the stimulation within a therapeutic window.

It will be appreciated that the algorithm 700 is an example of a template subtraction algorithm. Other examples of template subtraction algorithms exist in the art (some are described above), but they typically involve creating a template from the complete artifact, not just the residual as is described here. Such algorithms typically function by having an entire signal template stored in memory and then scaled per use, rather than storing just a few parameters to process part of the artifact as is described here.

Although particular embodiments of the present invention have been shown and described, the above discussion is not intended to limit the present invention to these embodiments. It will be obvious to those skilled in the art that various changes and modifications may be made without departing from the spirit and scope of the present invention.

Thus, the present invention is intended to cover alternatives, modifications, and equivalents that may fall within the spirit and scope of the present invention as defined by the claims.

What is claimed is:

1. A system for providing electrical stimulation to a patient's spinal cord using one or more electrode leads implantable in the patient's spinal column, each electrode lead comprising a plurality of spinal electrode contacts, the system comprising:

a neurostimulator that is connectable to the one or more electrode leads, and control circuitry configured to:

cause the neurostimulator to use one or more of the spinal electrode contacts to provide a first electrical stimulation to the patient's spinal cord, wherein the first electrical stimulation is configured to evoke a first stimulation artifact but not to evoke a detectable neural response in the patient's spinal cord, cause the neurostimulator to use a second one or more of the spinal electrode contacts to record a first signal comprising a first stimulation artifact component, fit the first signal to a mathematical model to yield a template signal, wherein the mathematical model comprises an exponential decay, cause the neurostimulator to use one or more of the spinal electrode contacts to provide second electrical stimulation to the patient's spinal cord, wherein the second electrical stimulation is configured to evoke a second stimulation artifact and a neural response in the patient's spinal cord, cause the neurostimulator to use a one or more of the spinal electrode contacts to record a second signal comprising a second stimulation artifact component and a neural response component, use the second signal and the template signal to determine a third signal, wherein the third signal comprises the neural response component and comprises a smaller stimulation artifact component than does the second signal, determine one or more features of the third signal, and use the one or more features of the third signal for closed loop feedback adjustment of therapeutic stimulation.

2. The system of claim 1, wherein the amplitude of the first electrical stimulation is less than the amplitude of the second electrical stimulation.

3. The system of claim 1, wherein using the second signal and the template to determine a third signal comprises scaling the template signal with respect to the second signal.

4. The system of claim 3, wherein using the second signal and the template to determine a third signal comprises subtracting the scaled template signal from the second signal to yield the third signal.

5. The system of claim 1, wherein the control circuitry is control circuitry of the neurostimulator.

6. The system of claim 1, wherein the control circuitry is control circuitry of an external computing device.

7. The system of claim 6, wherein the control circuitry is further configured to display a representation of the third signal on a graphical display of the external computing device.

8. The system of claim 1, wherein the therapeutic stimulation is the second electrical stimulation.

9. The system of claim 1, wherein the closed loop feedback adjustment is configured to maintain the therapeutic stimulation within a therapeutic window.

10. The system of claim 1, wherein the mathematical model comprises a term of the form $$V(t) = V_0 e^{\frac{-t}{\tau}},$$

where V(t) is voltage as a function of time t, $V_0$ is peak voltage, and $\tau$ is a decay time constant.

11. The system of claim 10, wherein the decay time constant t depends on the resistance R and capacitance C of tissue near the electrode contacts.

12. The system of claim 1, wherein the neural response is a compound evoked action potential (ECAP).

13. A method for providing electrical stimulation to a patient's spinal cord using one or more electrode leads implantable in the patient's spinal column, each electrode lead comprising a plurality of spinal electrode contacts, the method comprising:

using one or more of the spinal electrode contacts to provide a first electrical stimulation to the patient's spinal cord, wherein the first electrical stimulation is configured to evoke a first stimulation artifact but not to evoke a detectable neural response in the patient's spinal cord, using a second one or more of the spinal electrode contacts to record a first signal comprising a first stimulation artifact component, fitting the first signal to a mathematical model to yield a template signal, wherein the mathematical model comprises an exponential decay, using one or more of the spinal electrode contacts to provide second electrical stimulation to the patient's spinal cord, wherein the second electrical stimulation is configured to evoke a second stimulation artifact and a neural response in the patient's spinal cord, using a one or more of the spinal electrode contacts to record a second signal comprising a second stimulation artifact component and a neural response component, and using the second signal and the template signal to determine a third signal, wherein the third signal comprises the neural response component and comprises a smaller stimulation artifact component than does the second signal, determining one or more features of the third signal, and using the one or more features of the third signal for closed loop feedback adjustment of therapeutic stimulation.

14. The method of claim 13, wherein using the second signal and the template to determine a third signal comprises scaling the template signal with respect to the second signal and subtracting the scaled template signal from the second signal to yield the third signal.

15. The system of claim 13, wherein the mathematical model comprises a term of the form $$V(t) = V_0 e^{\frac{-t}{\tau}},$$

where V(t) is voltage as a function of time t, $V_0$ is peak voltage, and $\tau$ is a decay time constant wherein the decay time constant t depends on the resistance R and capacitance C of tissue near the electrode contacts.

16. The system of claim 13, wherein the control circuitry is further configured to determine one or more features of the third signal and to use the one or more features for closed loop feedback adjustment of therapeutic stimulation.

* * * * *